(12) United States Patent
Chen et al.

(10) Patent No.: US 7,783,096 B2
(45) Date of Patent: Aug. 24, 2010

(54) DEVICE SYSTEMS AND METHODS FOR IMAGING

(75) Inventors: Yunqiang Chen, Plainsboro, NJ (US); Hao Wu, Greenbelt, MD (US); Tong Fang, Morganville, NJ (US)

(73) Assignee: Siemens Corporation, Iselin, NJ (US)

( * ) Notice: Subject to any disclaimer, the term of this patent is extended or adjusted under 35 U.S.C. 154(b) by 861 days.

(21) Appl. No.: 11/675,258

(22) Filed: Feb. 15, 2007

(65) Prior Publication Data

US 2007/0196007 A1    Aug. 23, 2007

Related U.S. Application Data

(63) Continuation-in-part of application No. 11/548,863, filed on Oct. 12, 2006.

(60) Provisional application No. 60/727,576, filed on Oct. 17, 2005.

(51) Int. Cl.
*G06K 9/00* (2006.01)

(52) U.S. Cl. .................. 382/128; 382/131; 382/132

(58) Field of Classification Search ......... 382/128–134, 382/164, 165, 170, 192, 254, 255; 600/419, 600/420, 410, 437, 443, 449, 512, 431, 453, 600/507; 378/62, 98
See application file for complete search history.

(56) References Cited

U.S. PATENT DOCUMENTS 6,718,055 B1 * 4/2004 Suri ........................... 382/128
7,130,457 B2 * 10/2006 Kaufman et al. ............. 382/128

* cited by examiner

*Primary Examiner*—Vu Le
*Assistant Examiner*—Claire Wang

(57) ABSTRACT

Certain exemplary embodiments comprise a method, which can comprise determining an image of a predetermined physiological structure of a patient. The image can be determined based upon a first set of image data of the predetermined physiological structure of the patient. The image can be based upon a second set of image data of the predetermined physiological structure of the patient. The image can be determined based upon an iteratively adjusted movement of the patient.

19 Claims, 7 Drawing Sheets

DEVICE SYSTEMS AND METHODS FOR IMAGING

CROSS-REFERENCE TO RELATED APPLICATIONS

This application claims priority to, and incorporates by reference herein in its entirety, pending U.S. Provisional Patent Application Ser. No. 60/727,576, filed 17 Oct. 2005. This application is a continuation in part and claims priority to, and incorporates by reference herein in its entirety, pending U.S. patent application Ser. No. 11/548,863, filed 12 Oct. 2006.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
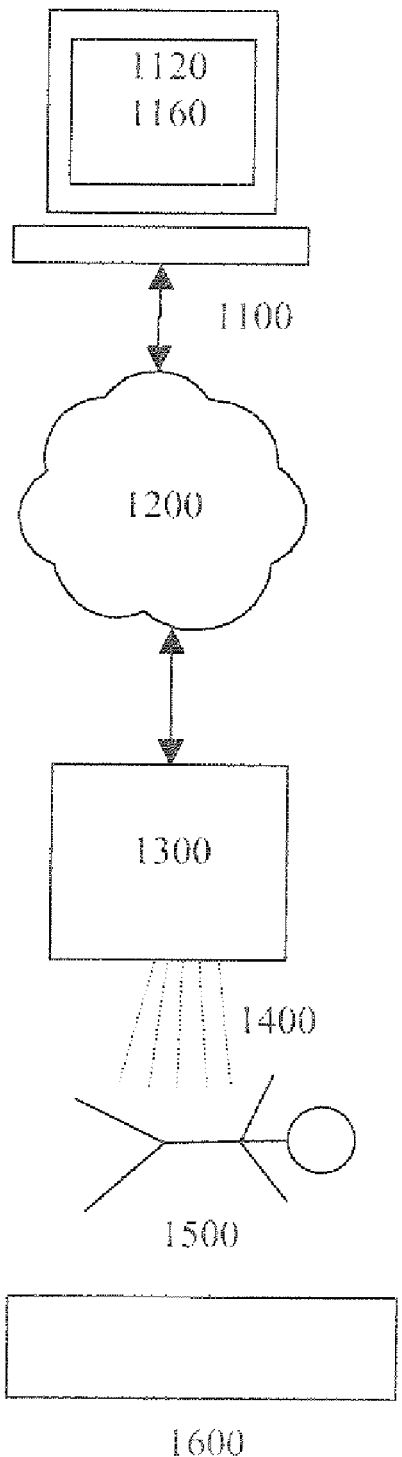
FIG. 1 is a block diagram of an exemplary embodiment of a system 1000.

Certain exemplary embodiments comprise a method, which can comprise determining an image of a predetermined physiological structure of a patient. The image can be determined based upon a first set of image data of the predetermined physiological structure of the patient. The image can be based upon a second set of image data of the predetermined physiological structure of the patient. The image can be determined based upon an iteratively adjusted movement of the patient.

Certain exemplary embodiments comprise a method, which can comprise determining an image of a bone-only or soft-tissue-only image of a predetermined physiological structure of a patient. The image can be determined based upon two sets of input images acquired with X-ray of different spectra on the predetermined physiological structure of the patient. The image can be determined based upon an iterative method to compensate the movement of the predetermined physiological structure of a patient during the acquisition of these two sets of images.

In certain exemplary embodiments, two images might be desired of a particular structure of a predetermined portion of an object, such as a physiological structure of a medical patient. In embodiments regarding the physiological structure of the medical patient, a bone only image that is substantially devoid of rendered soft tissue might be desired. Instead of and/or in addition to the bone only image, a soft tissue image might be desired that is substantially devoid of rendered bone. In certain exemplary embodiments, a relatively high energy spectrum can be used as an imaging technique to determine a first image, from which a substantially bone image can be obtained. In certain exemplary embodiments, a relatively low energy spectrum can be used as an imaging technique to determine a second image, from which a substantially soft tissue image can be obtained. The first image can comprise artifacts and/or a rather faint and/or blurry version of the second image, and/or the second image can comprise artifacts and/or a rather faint and/or blurry version of the first image. For example, the bone image can comprise soft tissue artifacts and/or the soft tissue image can comprise bone artifacts.

Certain exemplary embodiments can be adapted to utilize data associated with the first image to filter and/or subtract first image artifacts, structures, and/or elements from the second image and/or the second data associated with the second image to filter and/or subtract second image artifacts, structures and/or elements from the first image. In certain exemplary embodiments, the object, such as the patient, can be at a different location in the second image as compared to the first image. Such a movement can result in motion artifacts as data associated with the first image is used to filter and/or subtract first image motion artifacts from the second image and/or data associated with the second image is used to filter and/or subtract second image motion artifacts from the first image. Certain exemplary embodiments can be adapted to iteratively determine a best estimate of the movement of the object based upon an initial estimate of the first image and/or the second image. Certain exemplary embodiments can be adapted to utilize the best estimate of the movement of the object in an iterative determination of a best estimate of the first image and/or a best estimate of the second image.

The disclosure presents exemplary embodiments regarding X-ray imaging of patients. Additional embodiments can be realized in CT imaging, PET imaging, SPECT imaging, magnetic resonance imaging, radar imaging, laser imaging, sonar imaging, and/or any other imaging technology of animate and/or inanimate objects wherein images differ based upon energy and/or frequency spectra and image filtering and/or subtraction is desired, such as when physical movement of the object has occurred between the time the first image is generated and the time the second image is generated.

FIG. 1 is a block diagram of an exemplary embodiment of a system 1000, which can comprise an imaging device 1300. Imaging device 1300 can be any device adapted to provide an image, such as an image of a patient 1500. For example, imaging device 1300 can be an X-ray imaging device, and/or a computed tomography (CT) device. Imaging data can be obtained regarding patient 1500, such as via imaging device 1300, a device communicatively coupled thereto, and/or an independent detector 1600, utilizing reflected and/or absorbed emissions 1400 from imaging device 1300.

Imaging device 1300 and/or independent detector 1600 can be communicatively coupled to an information device 1100 directly and/or via a network 1200. Information device 1100 can comprise a user program 1160, which can be adapted to analyze, process, manage, align, and/or enhance image data from imaging device 1300. Information device 1100 can comprise a user interface 1120, which can be adapted to render image information associated with imaging device 1300.

Figure 2:
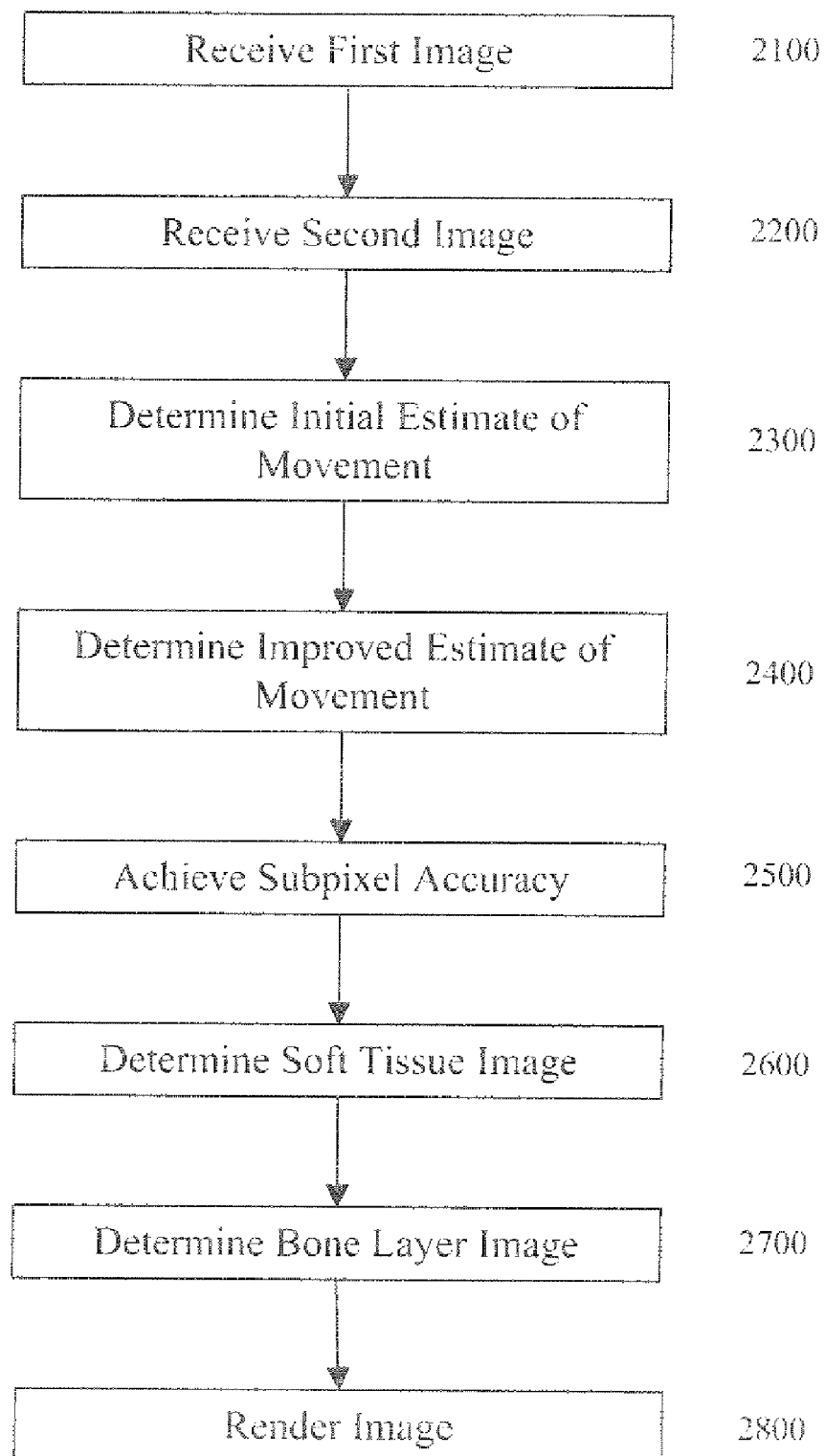
FIG. 2 is a flowchart of an exemplary embodiment of a method 2000.

FIG. 2 is a flowchart of an exemplary embodiment of a method 2000. At activity 2100, a first set of image data can be obtained and/or received from an imaging device, such as an X-ray device and/or a detector and/or an information device communicatively coupled thereto. The first set of image data can be of a predetermined physiological structure of a patient.

For example, the physiological structure can be a head, neck, foot, leg, thigh, pelvic region, hip region, torso, abdominal region, neck, and/or spinal column, etc. of the patient. The patient can be any animal, such as a human, horse, cow, dog, cat, dolphin, fish, monkey, antelope, and/or bear, etc. The first set of image data can originate from the X-ray device. The X-ray device can be operated at a first energy spectrum. The first set of image data can have originated during a first time interval.

At activity 2200, a second set of image data can be obtained and/or received from the imaging device. The second set of data can be of the predetermined physiological structure and can be received from the imaging device and/or the detector and/or the information device communicatively coupled thereto. The second set of image data can be of the predetermined physiological structure of the patient. The second set of image data can originate from the X-ray device. The X-ray device operated at a second energy spectrum. The second set of image data can have originated during a second time interval. The second time interval can be distinct from the first time interval.

At activity 2300, an initial estimate can be determined of a movement of the patient or a part thereof between the first time interval and the second time interval. The initial estimate can be determined via a corner matching based registration. The corner matching based registration can be determined via a method, which can comprise:

- defining a first Gaussian pyramid associated with the first image and/or defining a second Gaussian pyramid associated with the second image, the first Gaussian pyramid can comprise a plurality of layers, the second Gaussian pyramid can comprise a plurality of layers;
- calculating, such as automatically calculating, a first corner strength map, which can be associated with the first image;
- calculating, such as automatically calculating, a second corner strength map, which can be associated with the second image;
- initializing, such as automatically initializing, a rectangular mesh, which can be associated with each layer of the first Gaussian pyramid;
- for each control point in each rectangular mesh on a lowest resolution layer of the first Gaussian pyramid, automatically determining a point with a largest corner strength in a defined neighborhood and defining the point with the largest corner strength as the control point;
- for each control point of each mesh in the lowest resolution layer in the first Gaussian pyramid, automatically determining a corresponding control point in a corresponding layer in the second Gaussian pyramid; and/or
- generating, such as automatically generating, a corresponding mesh on each layer of the second Gaussian pyramid to each mesh associated with each layer of the first Gaussian pyramid, etc.

At activity 2400, an improved and/or refined estimate of the movement of the patient can be automatically determined. The movement of the patient can be a movement in the second time interval relative to the first time interval. The improved and/or refined estimate of the movement can be based upon the initial estimate of the movement. The improved estimate can be automatically obtained via an iterative hierarchical structured intensity comparison between the first Gaussian pyramid and the second Gaussian pyramid. The iterative hierarchical structured intensity comparison can comprise, from a lowest resolution layer to a highest resolution layer of the first Gaussian pyramid and the second Gaussian pyramid:

- defining a region-based, intensity invariant similarity measurement between the first image and the second image;
- attempting to estimate an optimal deformation, associated with each control point, that attempts to maximize a similarity between the first image and the second image by searching within a neighborhood of each control point;
- map an adjusted mesh of each layer to a next higher resolution layer to obtain an initial control point associated with the next higher resolution layer; and/or
- repeat the automatically determining the improved estimate activity for each resolution layer until the highest resolution layer is aligned, etc.

The estimated movement can be improved and/or refined via a mapped adjusted mesh of each layer of the plurality of layers. The plurality of layers can be iteratively mapped to obtain an initial control point associated with each next higher resolution level beginning at a lower layer and continuing through each of the plurality of layers of the first Gaussian pyramid and each of the plurality of layers of the second Gaussian pyramid until a highest resolution level of each of the first Gaussian pyramid and the second Gaussian pyramid is reached. A subpixel accuracy of the movement of the patient can be achieved via a subpixel search.

In certain exemplary embodiments, a movement between a given layer in the first Gaussian pyramid and a corresponding layer in the second Gaussian pyramid can be determined by attempting to minimize a functional:

$$\arg\min_{T^i}\left\{-CC(I_1^i, T^i(I_2^i)) + \lambda \sum_m \sum_n \left\|T^i(m, n) - \overline{T}_0^i(m, n)\right\|^2\right\}$$

where:

T is a transformation indicative of the movement of the patient in the second time interval relative to the first time interval;

CC is a region-based, intensity-invariant similarity measurement;

$I_1^i$ is an image associated with an $i^{th}$ layer of the first Gaussian pyramid based upon the first image;

$I_1^i$ is an image associated with an $i^{th}$ layer of the second Gaussian pyramid based upon the second image;

$T^i$ is a transformation indicative of a determined the movement of the patient in the second time interval relative to the first time interval associated with an ith layer of the first Gaussian pyramid and the second Gaussian pyramid;

$\lambda$ is a regularization parameter, m and n are indices of pixels in an $i^{th}$ layer of the first Gaussian pyramid; and $T_0$ is an initial estimate of the transformation indicative of the movement of the patient in the second time interval relative to the first time interval.

In certain exemplary embodiments, the movement can be estimated via a determination of the region-based, intensity-invariant similarity measurement, which can be obtained by evaluating a region-based, intensity-invariant similarity measurement based on an equation:

$$CC = \frac{\sum_m \sum_n (I_1(m,n) - \bar{I}_1) * (I_2(m,n) - \bar{I}_2)}{\sqrt{\sum_m \sum_n (I_1(m,n) - \bar{I}_1)^2 \sum_m \sum_n (I_2(m,n) - \bar{I}_2)^2}}$$

where:
CC is a correlation coefficient between predetermined neighborhoods of the first image and the second image;
$I_1$ is a target image;
$I_2$ is a source image;
$\bar{I}_1$ is an average intensity associated with the target image;
$\bar{I}_2$ is an average intensity associated with the source image; and
m and n are pixel indices.

At activity 2500, subpixel accuracy can be achieved in adjusting the first image and/or the second image. Subpixel accuracy can be achieved by searching within the neighborhood associated with each control point by utilizing a resolution level step size smaller than approximately one pixel on the highest resolution layer.

At activity 2600, a soft tissue image can be determined and/or estimated based on the estimated optimal deformation for each control point.

At activity 2700, a bone layer image can be determined and/or estimated based on the estimated optimal deformation for each control point.

At activity 2800, the adjusted, improved, and/or updated image of the predetermined physiological structure can be rendered, such as via a user interface. The adjusted and/or updated image can be of the bone layer and/or the soft tissue layer.

Image registration can be adapted to establish a spatial point-to-point correspondence between two images of a scene so that the two images can be directly compared, combined, subtracted, and/or analyzed, etc. Image registration can be used in applications such as change detection, data fusion, image mosaic development, and/or motion estimation, etc.

In medical imaging accurate and/or retrospective registration of images can be desirable. In certain exemplary embodiments, image registration can be utilized in dual energy subtraction chest radiography (DSR). Certain exemplary DSR applications acquire two images using low and high energy X-ray spectra respectively. The high energy X-ray spectra can be particularly useful for imaging soft tissue. The low energy X-ray spectra can be particularly useful for imaging bone tissue. Since the attenuation coefficients of bone and soft tissue follow different functions of energy, the two images can be weighted and then subtracted to generate cleaner soft tissue and bone structure in separated images. In certain exemplary embodiments, separated images might allow for better evaluations of lung nodules and/or pleural calcifications, etc.

In certain exemplary embodiments, an elapsed time between exposing the image from the low energy X-ray spectra and exposing the image from the high energy X-ray spectra can be approximately 300 milliseconds, during which patient or anatomical motions might result in significant motion artifacts. Although some patient related solutions and acquisition related solutions might provide a remedy in some cases, patient motion can occur in many situations, for example, some patients might have a sudden swallow or cough. In addition, a heart beating can result in motion artifacts in certain exemplary chest images. Certain exemplary embodiments can be adapted to correct motion artifacts retrospectively via an image registration technique.

According to a type of the distortion to be corrected between the image pair, image registration techniques can be divided into two categories: rigid registration and non-rigid registration. In certain exemplary embodiments, rigid registration techniques might not sufficiently compensate for unexpected patient motion in DSR. Certain exemplary embodiments can comprise a non-rigid registration algorithm for DSR images. A non-rigid registration algorithm can be decomposed into three components: a similarity measurement that can indicate how well two images match; a transformation model that can specify a manner in which a source image can be changed to match a target; and an optimization process that can change the transformation model to attempt to maximize a matching criterion. In certain exemplary embodiments, non-rigid registration can be based upon geometric matching based registration or intensity based registration.

In certain exemplary geometric matching based non-rigid registration methods, sparse features, such as edges, corners or manually selected anatomical landmarks, can be extracted and matched between the images; then one or more smooth interpolation methods can be used to interpolate between points to obtain a transformation model for whole images. In certain exemplary embodiments, interpolating between irregularly distributed sparse features can be based upon one or more spline based methods. Certain exemplary embodiments can utilize thin-plate splines and/or B-splines. In certain exemplary embodiments, an accuracy of geometric matching based methods can be influenced by accuracy and/or density of sparse features. In certain exemplary embodiments, geometric matching algorithms might not be automatic and might request user interaction to identify the landmarks. Even with accurate landmarks, certain exemplary geometric matching algorithms can have relative difficulty in finding an interpolation algorithm to get subpixel accuracy for a whole image, especially for a non-rigid case.

Certain exemplary algorithms can operate directly on image intensity grey values, without prior data reduction to geometric features. Intensity based registration algorithms can be divided into two groups: standard intensity-based registration and pair-and-smooth registration. Certain exemplary intensity based registration methods use an intensity similarity measurement to evaluate the accuracy of the registration. An intensity-based registration algorithm can attempt to minimize a combined energy function of intensity similarity term and smoothness constraint term at one stage, where the transformations are the same both in similarity term and in smoothness constraint term. Pair-and-smooth registration algorithms can use two separate transformations when attempting, respectively, to minimize an intensity similarity energy and smoothness penalty term.

Certain exemplary embodiments can comprise a non-rigid registration framework combining both a geometric matching method and an intensity based method for DSR image pairs. Certain exemplary embodiments can comprise a corner matching based registration to obtain a coarse non-rigid transformation model. Certain exemplary embodiments can then apply a regularized free-from intensity based registration to refine the transformation model. To reduce a probability of getting stuck in local minima and speed up convergence, the regularized free-from intensity based registration can be performed in a hierarchical structure, from coarse level to fine level, with flexibility to successively refine the transformation model to achieve subpixel accuracy.

In two-exposure DSR imaging, since bone structure and soft tissue can have different attenuation coefficients under different X-ray energy, certain exemplary embodiments the two images can be modeled as:

$$I_1 = a*B + b*S, \text{ and}$$

$$I_2 = c*T(B) + d*T(S),$$

where a,b,c,d are different constants relating to attenuation coefficients, which can be between 0 and 1; B is an image component due to bone structure and S is an image component due to soft tissue; T is a non-rigid deformation due to the patient breathing or other unexpected motion; $I_1$ is a reference image (target image); and $I_2$ is a moving image (source image). If no motion exists between the two DSR exposures, certain exemplary embodiments can multiply mathematical representations of the two images by appropriate weights and then subtract one from the other to obtain a bone specific image and a soft tissue specific image as:

$$B = (d*I_1 - b*I_2)/(a*d - b*c)$$

$$S = (a*I_2 - c*I_1)/(a*d - b*c).$$

Certain exemplary embodiments might assume a*d−b*c is positive. Since differences between the attenuation coefficients can be small, a*d−b*c can often be much smaller than 1. If there is motion between the two exposures and the retrospective registration is not accurate enough, model accuracy can be worse than in some other applications such as data fusion.

Suppose a pixel in one DSR image has gray value $I_1(i, j)$, a correct correspondence of the pixel in the other DSR image can be expressed as $I_2(k,l)$ due to some motion, if the correspondence is mismatched to $I_2(m,n)$, the error for subtracted bone intensity can be expressed as:

$$\varepsilon_{sub} = \begin{bmatrix} d*I_1(i, j) - b*I_2(m, n) - \\ d*I_1(i, j) + b*I_2(k, l) \end{bmatrix} / (a*d - b*c)$$

$$= \frac{b}{a*d - b*c} * [I_2(k, l) - I_2(m, n)],$$

where $\varepsilon_{sub}$ is a subtracted bone intensity error.

In certain exemplary embodiments, in DSR, b/(a*d−b*c) can be several times larger than 1, therefore if there is some error of the position correspondence, the error can be significantly enlarged and the subtracted results can be degraded. Subpixel accuracy can improve DSR images relative to other embodiments.

In a DSR image pair, the intensity might not be constant. Even with no motion, corresponding pixel pairs can have different intensities. Characteristics of certain exemplary DSR image pairs can be considered as being between monomodal and multi-modal. Therefore, certain similarity measurements used in mono-modal image registration, like sum of squared differences (SSD) or correlation coefficient (also known as normalized cross-correlation, NCC), might not be amenable to direct use for DSR image pairs. Certain similarity criteria used in multi-modal registration, such as mutual information, might not be sensitive enough for accurate locating. Some measurements based on a binary edge map can give a good evaluation of a similarity between the DSR image pair, however, obtaining a good binary edge map might not be easy, especially since thresholds for the two images can be relatively difficult to determine in order to obtain two edge maps with similar abundant structure details; also edge information might not be available in smooth regions. During experiments, it was observed that if the image was divided into small blocks, in most blocks, only one texture type, either from bone structure or from soft tissue, was dominant, which implied that one of soft tissue or bone tissue might be nearly constant in a small block, assuming soft tissue has no texture in a particular block, with no motion, images can be expressed as:

$$I_1^b = a*B + b*s$$

$$I_2^b = c*B + d*s,$$

where $I_1$ is a reference image for a block b (target image); and $I_2$ is a moving image for the block b (source image). In certain exemplary embodiments, the intensity of the two corresponding blocks can have a linear relationship; therefore, a correlation coefficient can be used as the similarity measurement for small blocks:

$$CC = \frac{\sum_m \sum_n (I_1(m, n) - \bar{I}_1) * (I_2(m, n) - \bar{I}_2)}{\sqrt{\sum_m \sum_n (I_1(m, n) - \bar{I}_1)^2 \sum_m \sum_n (I_2(m, n) - \bar{I}_2)^2}},$$

where $\bar{I}_1$ is an average intensity for the reference image and $\bar{I}_2$ is an average intensity for the moving image.

Certain exemplary intensity based non-rigid registration algorithms can be based upon an initial position and can properly converge, a pre-rigid-registration can be utilized before taking a non-rigid registration to compensate for a large translation, rotation or scale change. In certain exemplary embodiments, when a non-rigid distortion is large or complex, a remaining distortion for some pixels after rigid registration can still be large enough to make a non-rigid registration algorithm get stuck in a local minima or converge slowly. A hierarchical strategy can relieve this problem to some degree. To further reduce a probability of this problem, certain exemplary embodiments can utilize a corner based non-rigid registration first to get a better initial transformation model.

In certain exemplary embodiments, a Harris corner detector can be utilized to find the points with large corner strength in the reference image. The Harris corner detector can be based on a local structure matrix (Tensor), which can be utilized to compute a locally averaged moment matrix from image gradients. Eigenvalues of the moment matrix can be combined to calculate a corner strength measurement. A large value of the corner strength measurement can indicate a large probability of a corner position.

The local structure matrix (tensor) can be expressed as:

$$G = w_G(\sigma) * \begin{bmatrix} I_x^2 & I_x I_y \\ I_x I_y & I_y^2 \end{bmatrix} = \begin{bmatrix} \bar{I}_x^2 & \bar{I}_x \bar{I}_y \\ \bar{I}_x \bar{I}_y & \bar{I}_y^2 \end{bmatrix},$$

where: G is the local structure matrix (tensor),
$I_x$ and $I_y$ are derivatives of the image,
$w_G$ is a low-pass filter kernel such as Gaussian-shaped kernel,
σ is the size of the Gaussian-shaped kernel, $\tilde{I}_x$ is image gradient (derivative) in a horizontal direction,
$\tilde{I}_y$ is image gradient (derivative) in a vertical direction.

If desired, the image can be smoothed before taking derivative. The entries of G can be calculated and smoothed by a Gaussian filter ($w_G$) or just simply averaged in a local neighborhood. The local structure matrix can be symmetric and can have two non-negative eigenvalues: $\lambda_1$ and $\lambda_2$. The eigenvalues and eigenvectors can have a geometric interpretation, roughly the eigenvectors can be orthogonal to edges, and corresponding eigenvalues can be proportional to contrast in the direction of the eigenvector. Therefore, a corner can be identified as a location where both eigenvalues are large. The measurement of corner strength can be defined as:

$$C(G) = \det(G) - k \ast \text{trace}^2(G)$$

where k is suggested to 0.04. In certain exemplary embodiments, a different estimate can be utilized that avoids choosing the appropriate parameter k:

$$C(G) = \det(G)/\text{trace}(G).$$

In terms of the entries of G, the above measurement can be expressed as:

$$C(G) = (\tilde{I}_x^2 \tilde{I}_y^2 - (\tilde{I}_x \tilde{I}_y)^2)/(\tilde{I}_x^2 + \tilde{I}_y^2 + \epsilon),$$

where $\epsilon$ is a small constant to avoid dividing by zero. This definition was used in experimental verifications of certain exemplary embodiments.

In certain exemplary geometric matching based registration, sparse features can be extracted from each of a pair of DSR images; then these two sets of features can be matched to each other by using Iterative Closes Point (ICP) like algorithms; after that some smooth interpolation methods can be applied to obtain the transformation model. This procedure can be relatively complex and/or time consuming. Geometric based registration can be used to obtain a relatively good approximation of the transformation model.

Certain exemplary embodiments can convert irregularly distributed sparse features into regular control points, like the control points of a rectangle mesh, thus, the interpolation step can be avoided. Furthermore, since the good feature points might not be easy to obtain in practice, instead of matching between two sets of feature points, block matching can be used to search a correspondence of feature points between two DSR images. Based on some prior knowledge, a maximal distortion can be estimated in terms of a displacement from an original position after global rigid registration, usually for DSR image pairs, global rigid registration can be skipped due to the relative small distortion in a short period; then certain exemplary embodiments can search around features in a neighborhood to find best matches.

In certain exemplary embodiments, block matching might not be sufficiently reliable when the block matching lacks texture around regularly distributed control points. To improve a result, a closest corner point can be used to substitute the control point to do block matching. Under the smooth assumption of the deformation, a difference between a motion of a corner point and a control point can be very small. The displacement of the control point to the corresponding corner point can be mapped to obtain an initial non-rigid transformation model denoted by two rectangle meshes.

Certain exemplary embodiments can comprise method that comprises:
building two N level Gaussian Pyramids $G_{I_1}$, $G_{I_2}$ for image $I_1$ and $I_2$ respectively;
if desired, low pass filtering can be performed;
calculating a corner strength map $C(G_{I_1}(N))$ for $G_{I_1}(N)$, where $G_{I_1}(N)$ is a coarsest level of $G_{I_1}$;
initializing a rectangular mesh $M_1^N(p,q), p \in [1,P], q \in [1,Q]$ used for geometric registration for $G_{I_1}(N)$;
for each control point in $M_1^N$, finding a point with largest corner strength in some defined small neighborhood, denote it as the control point $Ctr(p,q), p \in [1,P], q \in [1,Q]$;
via a block matching method, finding the correspondence of each control point in $G_{I_2}(N)$, which can be denoted as $Ctr'(p,q)$;
computing a correspondent mesh $M_2^N(p,q) = M_1^N(p,q) + Ctr'(p,q) - Ctr(p,q)$, where $p \in [1,P], q \in [1,Q]$; and/or
via initial non-rigid transformation models $M_1^N$ and $M_2^N$ refining the registration, etc.

Image registration can be an ill-posed problem. In a solution space, many indistinguishably good answers can exist. In non-rigid registration, solutions can exist in a large dimensional (such as a combinatorially intractable discrete) space. In certain exemplary embodiments, a Tikhonov regularization method can be used to solve an ill-posed problem. By constraining a solution derivative's energy, solutions can be restricted to a computable subspace with provable uniqueness. The Tikhonov regularization method can result in solutions that are physically meaningful. Optical flow can be considered as a fast mono-modal non-rigid registration method. Certain exemplary non-rigid registration algorithms can be based on optical flow calculations. However, in DSR, the intensity of the two images might not satisfy a constant intensity assumption of optical flow. Accordingly, the standard intensity-based non-rigid registration algorithms can attempt to minimize an energy function:

$$E(T) = E_{sim}(I_1, I_2, T) + \lambda E_{reg}(T)$$

where:
E(T) is the energy function;
$E_{sim}$ is a similarity energy,
T is a transformation,
$\lambda$ is a regularization parameter, and
$E_{reg}(T)$ is a regularization energy.

This resulting optimization criterion can also be formulated with Bayesian theory:

$$P(T | I_1, I_2, T_0) = \frac{P(I_1, I_2 | T, T_0) P(T | T_0)}{P(I_1, I_2 | T_0)},$$

where $T_0$ is the prior knowledge about T. Taking a log of the above formula results in:

$$\log P(T|I_1,I_2,T_0) = \log(I_1,I_2|T,T_0) + \log P(T|T_0) - \log P(I_1,I_2|T_0)$$

where $\log P(I_1,I_2|T_0)$ is a constant term with respect to T, which can be dropped during an optimization process. Therefore, to find the optimal T an attempt can be made to maximize $\log P(T|I_1,I_2,T_0)$. However, in practice, calculating probabilities on the right hand side of this equation can be challenging.

The probability $P(I_1,I_2|T,T_0)$ can be inversely proportional to a difference between $I_1$ and $T(I_2)$; while $P(T|T_0)$ can be inversely proportional to a difference between T and $T_0$. In certain exemplary embodiments, based on such an analysis, the difference between $I_1$ and $T(I_2)$ can be computed as:

$$E_{sim}(I_1, I_2, T) = \sum_i \min_{\alpha,\beta} \left( \sum_m \sum_n [I_1(m,n) - \alpha T_i(I_2)(m,n) - \beta]^2 \right),$$

where:
- α and β are unknown linear transformation parameters (scaling and shifting) between intensities of corresponding pixels of the first image and the second image,
- $I_1$ is the first image,
- $I_2$ is the second image,
- m is the x coordinate, and
- n is the y coordinate.

Since for DSR image pairs, the linear intensity relationship might hold only inside a small block, certain exemplary embodiments can divide an image into small blocks and sum the difference over all small blocks. Furthermore, by using correlation coefficient, the following formula can apply:

$$\arg\min_T E_{sim}(I_1, I_2 | T, T_0) = \arg\max_T \sum_i CC(I_1^i, T^i(I_2^i))$$

where;
- $T_0$ is a motion estimation projected from coarser level (i.e. $(i-1)^{th}$ level) in a pyramid, and
- $T^i$ is the transformation on $i^{th}$ level in the pyramid.

Certain exemplary embodiments can apply a smoothness penalty to compute the second term;

$$E_{reg}(T) = \iint \|dT\|^2$$

Certain exemplary embodiments can be iteratively executed in a pyramid hierarchical structure, from coarse level to fine level, other prior information can be obtained from a former iteration besides a smoothness constraint. That is the transformation model in a current iteration might not differ much from the result of the former iteration. Therefore, the second term can be calculated as follows:

$$E_{reg}(T | T_0) = \sum_i \sum_j \|dT(i,j)\|^2 + \sum_i \sum_j \|T(i,j) - T_0(i,j)\|^2$$

$$= \sum_i \sum_j \|T(i,j) - \overline{T}(i,j)\|^2 + \sum_i \sum_j \|T(i,j) - T_0(i,j)\|^2$$

$$= \sum_i \sum_j \begin{bmatrix} 2T^2(i,j) + \overline{T}^2(i,j) + T_0^2(i,j) - \\ 2T(i,j)\overline{T}(i,j) - 2T(i,j)T_0(i,j) \end{bmatrix}$$

$$\cong \sum_i \sum_j \begin{bmatrix} 2T^2(i,j) + \overline{T}_0^2(i,j) + T_0^2(i,j) - \\ 2T(i,j)\overline{T}_0(i,j) - 2T(i,j)T_0(i,j) \end{bmatrix}$$

$$\cong \sum_i \sum_j \begin{bmatrix} 2T^2(i,j) + \overline{T}_0^2(i,j) + \overline{T}_0^2(i,j) - \\ 2T(i,j)\overline{T}_0(i,j) - 2T(i,j)\overline{T}_0(i,j) \end{bmatrix}$$

$$= \sum_i \sum_j \|T(i,j) - \overline{T}_0(i,j)\|^2$$

In certain exemplary embodiments, T(i, j) can be updated sequentially rather than in a batch. Hence, $\overline{T}(i,j)$ might not be computed during an update. Certain exemplary embodiments can use $T_0(i, j)$ to substitute T(i, j) in a first approximation; based on an assumption that the current transformation model should be similar to the previous one. In a second approximation, a smoothness constraint of $T_0$ can be used such that $T_0(i,j) \cong \overline{T}_0(i,j)$.

In certain exemplary embodiments, since $E_{sim}$ is an intensity similarity measurement, while $E_{reg}$ is a geometric measurement, $E_{sim}$ and $E_{reg}$ might not have the same physical dimension. In certain exemplary embodiments, a trade-off parameter can be relatively difficult to set. In certain exemplary embodiments, to make the trade-off parameter more stable across different images, $E_{reg}$ can be placed into a Gaussian function $g(\overline{T}_0(i,j), \sigma)$ to get a normalized evaluation, where σ can have a physical interpretation, which can depend on a smoothness of the transformation model. Hence, the two energy terms can be numerically compatible and the trade-off parameter can be relatively stable across different images.

In certain exemplary embodiments, an optimization criterion for DSR image pairs can be expressed as:

$$\arg\min_T \left\{ -\sum_i CC(I_1^i, T^i(I_2^i)) + \lambda \sum_m \sum_n \|T(m,n) - \overline{T}_0(m,n)\|^2 \right\}$$

An exemplary free-form intensity based registration can comprise, for each level k in a Gaussian Pyramid, k from coarse (N) to fine (0), do the following:
- for each control point $M_2^k$ (p,q), find a local minimum of previous objective functional via searching around the neighborhood of that control point, if desired, repetitively;
- map an adjusted mesh $M_2^k$ to a next high resolution level to get initial $M_2^{k-1}$, refine the mesh if desired;
- repeat the above procedure until acceptable results are attained, then use a motion estimate at a finest layer (i.e., $M_1^0$ and $M_2^0$) to register $I_2$ to $I_1$ and do weighted subtraction to get bone and soft tissue images.

In certain exemplary embodiments, subpixel accuracy can be achieved by interpolating a distance measure or by interpolating images. In certain exemplary embodiments, relative difficulty might be experienced in finding a subpixel minimum of the distance measure at integer displacements in a two-dimensional case. Finding the subpixel minimum might be relatively complex when a search range is large. Certain exemplary embodiments can attain subpixel precision via interpolating images via linear interpolation, which can be relatively good for re-sampling. Since a regular rectangle reference mesh can be used, bilinear interpolation can be used both for geometric position interpolation and intensity interpolation. Certain exemplary embodiments can change an interpolation method in order to achieve subpixel accuracy. Certain exemplary embodiments can reduce the search step successively to achieve expected precision.

Figure 4:
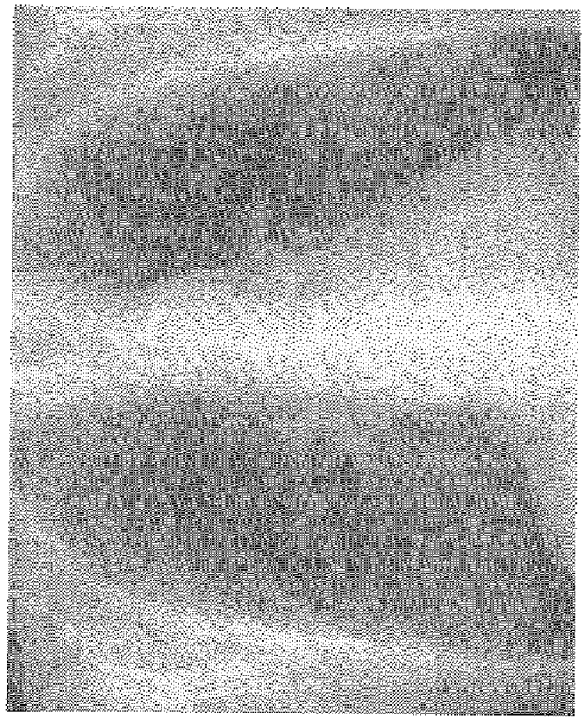
FIG. 4 is an exemplary embodiment of an X-ray image.
Figure 3:
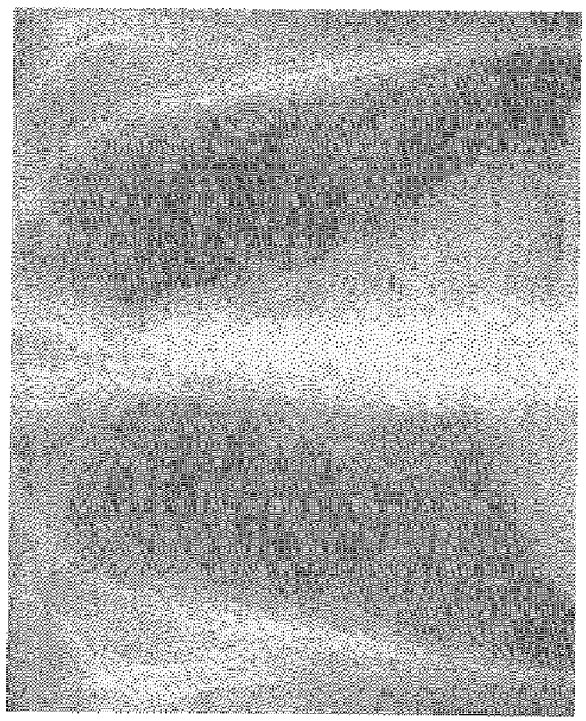
FIG. 3 is an exemplary embodiment of an X-ray image.

An exemplary algorithm was tested via exemplary generated data. $I_2$ was warped by a smooth non-rigid deformation, which simulated a breathing effect and a rigid deformation of translation and rotation. Without registration before subtraction, the results appeared to degenerate significantly:

FIGS. 3 and 4 are exemplary embodiments of X-ray images, which can be DSR images. FIG. 3 was exposed at a first X-ray energy level at a first time. FIG. 4 was exposed at a second X-ray energy level at a second time. As illustrated, FIG. 4 appears to have translation, rotation, and non-rigid displacement with respect to FIG. 3.

Figure 6:
FIG. 6 is an exemplary embodiment of an X-ray image.
Figure 5:
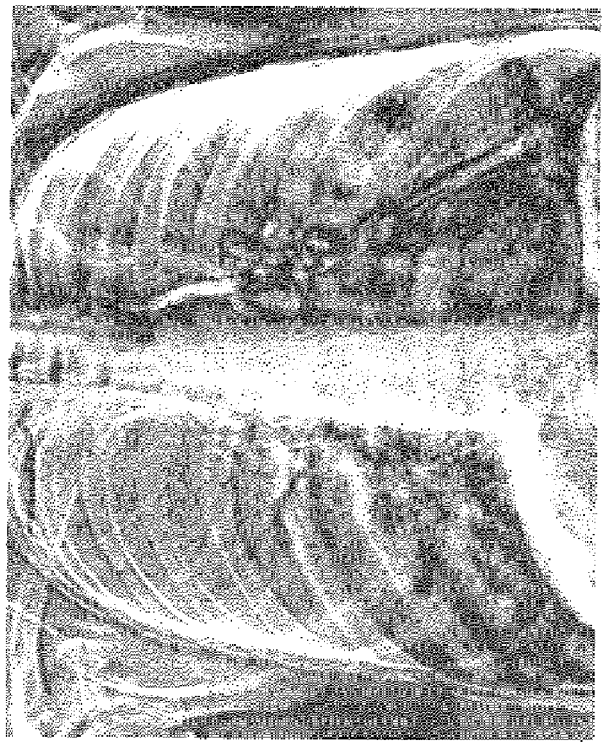
FIG. 5 is an exemplary embodiment of an X-ray image.

FIGS. 5 and 6 are exemplary embodiments of X-ray images, which illustrate a directly subtracted bone image in FIG. 5 and a soft tissue image in FIG. 6, each of which appeared to be degenerated significantly. Each of the bone image and the soft tissue image were derived from the pair of X-ray images of FIGS. 3 and 4.

Figure 8:
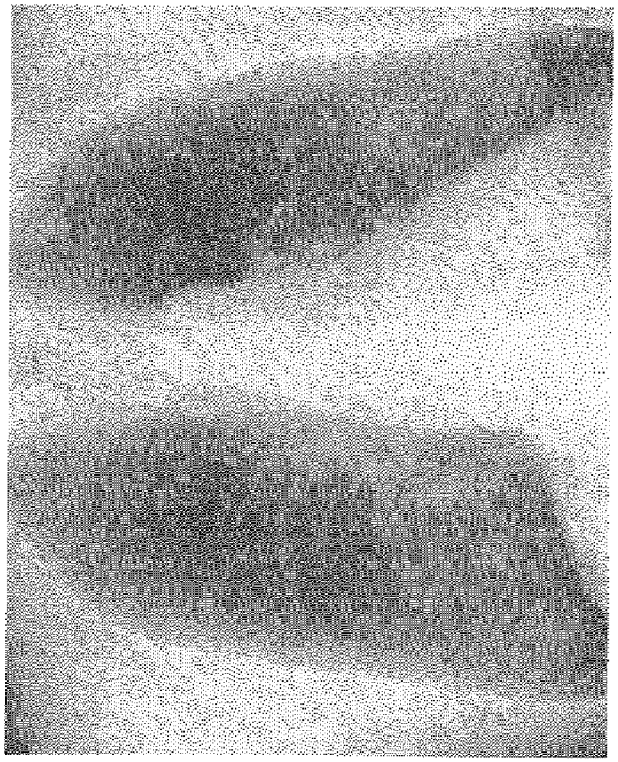
FIG. 8 is an exemplary embodiment of an X-ray image.
Figure 7:
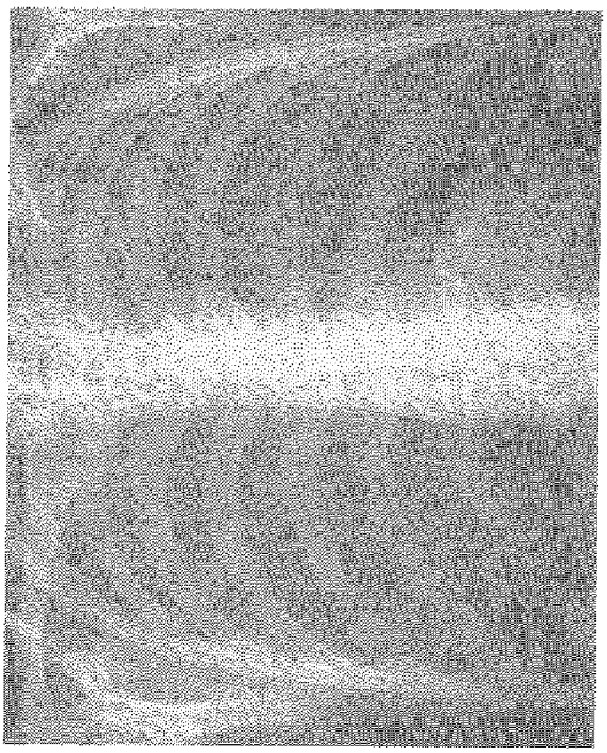
FIG. 7 is an exemplary embodiment of an X-ray image.

FIGS. 7 and 8 are exemplary embodiments of X-ray images, which illustrate a subtracted bone image and a soft image after registration. Each of the subtracted bone image and the soft tissue image after registration were derived from the pair of X-ray images of FIGS. 3 and 4.

Figure 10:
FIG. 10 is an exemplary embodiment of an X-ray image.
Figure 9:
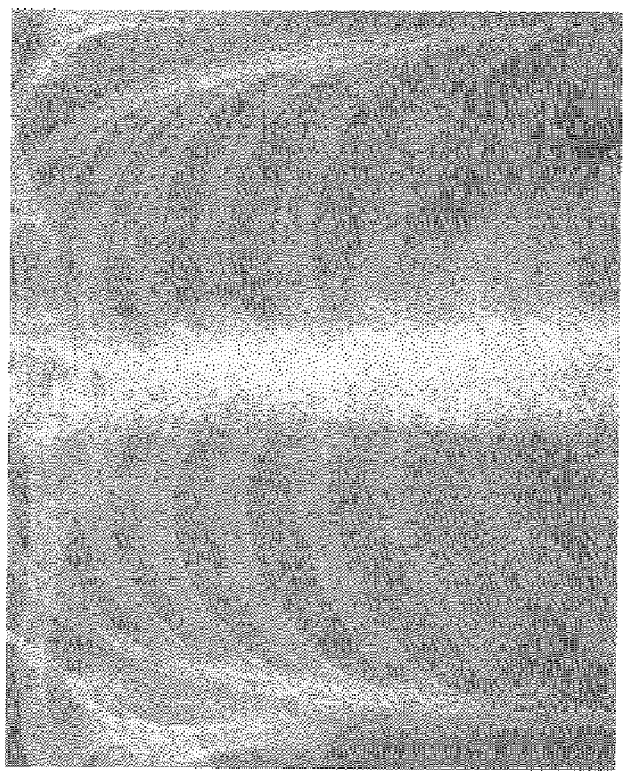
FIG. 9 is an exemplary embodiment of an X-ray image.

FIGS. 9 and 10 are exemplary embodiments of X-ray images, which illustrate a ground truth bone image and a ground truth soft tissue image for the pair of X-ray images of FIGS. 3 and 4.

Figure 11:
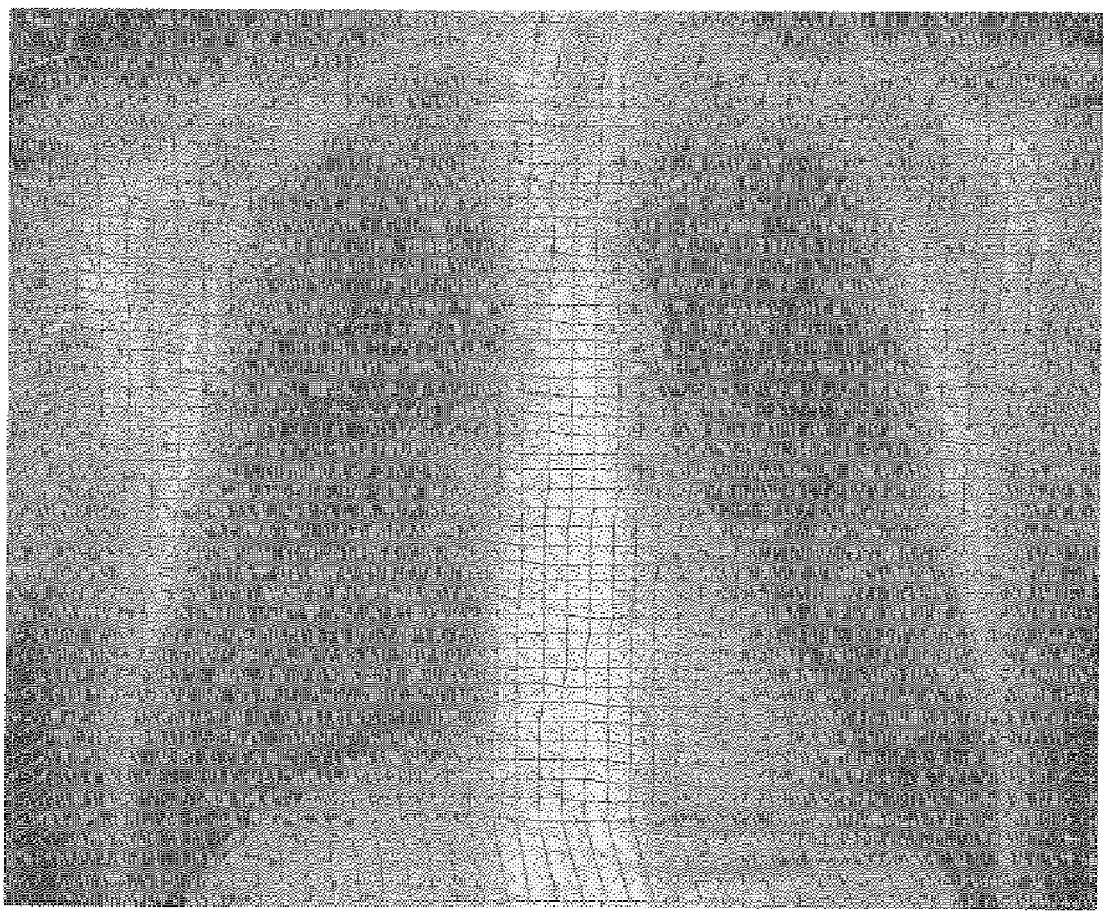
FIG. 11 is an exemplary illustration of a mesh used for image registration.

FIG. 11 is an exemplary illustration of a mesh used for image registration, which illustrates the final mesh used for registration. The blue line shows the result of the exemplary algorithm and the red line represents ground truth. The average error of the control points was 0.1587 pixels, the variance of the error was 0.0185 pixels, and the maximum error was 1.0220 pixels. The finest search step was 0.125 pixels.

Certain exemplary embodiments provide a combined non-rigid registration algorithm for DSR image pairs. In order to find a good initial transformation model for intensity based non-rigid registration algorithm, a fast corner based geometric non-rigid registration can be utilized to get an initial non-rigid transformation model. Compare to rigid pre-registration, the presented corner based non-rigid registration can give a better approximation of the transformation model, which helps a subsequent intensity based registration to converge faster and avoid getting stuck in local minima. In certain exemplary embodiments, a Gaussian pyramid hierarchical structure can be adopted in an intensity based registration algorithm. By using full image content, an exemplary regularized free-form non-rigid registration can achieve subpixel accuracy. Experimental results demonstrated that an exemplary combined algorithm was relatively efficient and accurate. Except for DSR image registration, certain exemplary embodiments can also be used for other image registration with some change to the similarity measurement.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
activity—an action, act, deed, function, step, and/or process and/or a portion thereof.
achieve—to attain with effort.
adapted to—suitable, fit, and/or capable of performing a specified function.
adjust—to change so as to match, fit, adapt, conform, and/or be in a more effective state.
algorithm—a method and/or procedure adapted to solve a problem and/or perform a function.
align—to adjust substantially into a proper orientation and location with respect to another thing.
and/or—either in conjunction with or in alternative to.
apparatus—an appliance or device for a particular purpose.
approximately—about and/or nearly the same as.
around—in all directions from a point of reference.
associate—to relate, bring together in a relationship, map, combine, join, and/or connect.
associated with—related to.
at least—not less than.
attempt—to try to achieve.
automatically—acting and/or operating in a manner essentially independent of external human influence and/or control. For example, an automatic light switch can turn on upon "seeing" a person in its view, without the person manually operating the light switch.
average—a value obtained by dividing the sum of a set of quantities by the number of quantities in a set and/or an approximation of a statistical expected value.
based upon—determined in consideration of and/or derived from.
beginning—a starting point.
below—less than.
between—in a separating interval and/or intermediate to.
beyond—more distant than.
bone layer—a representation of bone, the representation substantially devoid of a representation of soft tissue.
calculate—to determine via mathematics and/or logical rules.
can—is capable of, in at least some embodiments.
cause—to bring about, provoke, precipitate, produce, elicit, be the reason for, result in, and/or effect.
characteristic—a distinguishing feature.
comprises—includes, but is not limited to, what follows.
comprising—including but not limited to, what follows.
configure—to design, arrange, set up, shape, and/or make suitable and/or fit for a specific purpose.
constant—continually occurring; persistent; and/or unchanging.
constraint—a limitation.
continue—to go on with a particular action, to carry on, and/or to resume.
control point—a defined image location based upon which the image can be moved and/or adjusted.
corner matching based registration—a method converting a plurality of images to a common coordinate system based upon attempting to locate a common feature near intersections of edges in each of the plurality of images and using the common feature as a reference point for the common coordinate system.
corner strength map—a representation of an image based upon dividing the image into a plurality of neighborhoods and determined strengths of corners of each of the plurality of neighborhoods based upon a locally averaged moment matrix computed from intensity gradients of the image and combined eigenvalues of the moment matrix.
correct—to remedy, adjust in value, and/or change to a more desired value.
correlation coefficient—a value indicative of a degree to which two variables are associated with each other.
corresponding—related, associated, accompanying, similar in purpose and/or position, conforming in every respect, and/or equivalent and/or agreeing in amount, quantity, magnitude, quality, and/or degree.
create—to make, form, produce, generate, bring into being, and/or cause to exist.
data—information represented in a form suitable for processing by an information device.
data structure—an organization of a collection of data that allows the data to be manipulated effectively and/or a logical relationship among data elements that is designed to support specific data manipulation functions. A data structure can comprise metadata to describe the properties of the data structure. Examples of data structures can include: array, dictionary, graph, hash, heap, linked list, matrix, object, queue, ring, stack, tree, and/or vector.

define—to establish the meaning, relationship, outline, form, and/or structure of; and/or to precisely and/or distinctly describe and/or specify.
denote—to indicate.
dependent—relying upon and/or contingent upon.
determination—an act of making or arriving at a decision.
determine—to obtain, calculate, decide, deduce, establish, and/or ascertain.
device—an instrumentality adapted to a particular purpose.
distinct—discrete and/or readily distinguishable from all others.
during—at some time in a time interval.
each—every one of a group considered individually.
edge—a border at which a surface terminates.
energy—usable power.
equation—a determinable mathematical expression.
estimate—(v.) to calculate and/or determine approximately and/or tentatively; (n.) a value calculated and/or determined approximately and/or tentatively.
evaluate—to determine a value of.
factor—a criteria and/or something that contributes to a cause of an action.
first—before some other thing in an ordering.
fourth—following a third thing in an ordering.
from—used to indicate a source.
functional—a defined mathematical relationship.
further—in addition.
Gaussian pyramid—a hierarchy of Gaussian-shaped low-pass filtered and downsampled versions of an original image.
generate—to create, produce, render, give rise to, and/or bring into existence,
haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.
hierarchical structured intensity comparison—a determination of similarities and/or differences between strengths and/or sharpnesses of image neighborhoods between levels (i.e., layers) of a defined, layered image abstraction such as a Gaussian pyramid.
higher—greater than in an ordering.
highest—greatest in an ordering.
if—in case that.
image—an at least two-dimensional representation of an entity and/or phenomenon. The representation of the entity and/or phenomenon can be a mathematical representation and/or a visually discernible representation.
improve—to cause to be in a more desired state or condition.
indicate—to show, mark, signal, signify, denote, evidence, evince, manifest, declare, enunciate, specify, explain, exhibit, present, reveal, disclose, and/or display.
indicative—serving to indicate.
indicator—one or more signs, tokens, symbols, signals, devices, and/or substance that indicates.
indices—a plurality of counting variables.
information—facts, terms, concepts, phrases, expressions, commands, numbers, characters, and/or symbols, etc., that are related to a subject. Sometimes used synonymously with data, and sometimes used to describe organized, transformed, and/or processed data. It is generally possible to automate certain activities involving the management, organization, storage, transformation, communication, and/or presentation of information.
information device—any device on which resides a finite state machine capable of implementing at least a portion of a method, structure, and/or or graphical user interface described herein. An information device can comprise well-known communicatively coupled components, such as one or more network interfaces, one or more processors, one or more memories containing instructions, one or more input/output (I/O) devices, and/or one or more user interfaces (e.g., coupled to an I/O device) via which information can be rendered to implement one or more functions described herein. For example, an information device can be any general purpose and/or special purpose computer, such as a personal computer, video game system (e.g., PlayStation, Nintendo Gameboy, X-Box, etc.), workstation, server, minicomputer, mainframe, supercomputer, computer terminal, laptop, wearable computer, and/or Personal Digital Assistant (PDA), iPod, mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, a digital signal processor, an ASIC or other integrated circuit, a hardware electronic logic circuit such as a discrete element circuit, and/or a programmable logic device such as a PLD, PLA, FPGA, or PAL, or the like, etc.
initial—at a beginning.
initialize—to create, produce, render, give rise to, and/or bring into existence.
input/output (I/O) device—an input/output (I/O) device of an information device can be any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.
interpolation—estimating a value located numerically between two known values.
iteration—a repetition.
iterative—repeatedly.
iteratively—repetitively.
knowledge—the ability to interpret information in order to extract greater meaning.
largest—greatest in magnitude.
layer—a level of a representation of an image.
less than—having a measurably smaller magnitude and/or degree as compared to something else.
level—a relative position on a scale and/or a position along a vertical axis indicating height and/or depth.
located—situated in a particular spot and/or position.
location—a place.
lower—smaller in an ordering.
lowest—smallest in an ordering.

machine instructions—directions adapted to cause a machine, such as an information device, to perform one or more particular activities, operations, and/or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine-readable medium—a physical structure from which a machine, such as an information device, computer, microprocessor, and/or controller, etc., can obtain and/or store data, information, and/or instructions. Examples include memories, punch cards, and/or optically-readable forms, etc.

map—(n.) a logical association of values of one variable with values of a different variable; (v.) to represent or delineate on or as if on a map and/or to relate, correlate, and/or associate specified entities.

mathematical representation—an approximation, equivalent, and/or characterization of something based upon a defined action, behavior, procedure, and/or functional relationship.

maximize—to obtain a highest possible value of one or more variable quantities.

may—is allowed and/or permitted to, in at least some embodiments.

measure—(n) a quantity ascertained by comparison with a standard. (v) to physically sense, and/or determine a value and/or quantity of something relative to a standard.

medical—of or relating to the study or practice of medicine.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

minimize—to attempt to reduce in magnitude.

movement—a change in position from one location to another.

move—to transfer from one location to another.

mutual—pertaining to each of two or more things.

neighborhood—a region close, adjacent, and/or approximately adjacent to a defined location.

network—a communicatively coupled plurality of nodes, communication devices, and/or information devices. Via a network, such devices can be linked, such as via various wireline and/or wireless media, such as cables, telephone lines, power lines, optical fibers, radio waves, and/or light beams, etc., to share resources (such as printers and/or memory devices), exchange files, and/or allow electronic communications therebetween. A network can be and/or can utilize any of a wide variety of sub-networks and/or protocols, such as a circuit switched, public-switched, packet switched, connection-less, wireless, virtual, radio, data, telephone, twisted pair, POTS, non-POTS, DSL, cellular, telecommunications, video distribution, cable, terrestrial, microwave, broadcast, satellite, broadband, corporate, global, national, regional, wide area, backbone, packet-switched TCP/IP, IEEE 802.03, Ethernet, Fast Ethernet, Token Ring, local area, wide area, IP, public Internet, intranet, private, ATM, Ultra Wide Band (UWB), Wi-Fi, BlueTooth, Airport, IEEE 802.11, IEEE 802.11a, IEEE 802.11b, IEEE 802.11g, X-10, electrical power, multi-domain, and/or multi-zone sub-network and/or protocol, one or more Internet service providers, and/or one or more information devices, such as a switch, router, and/or gateway not directly connected to a local area network, etc., and/or any equivalents thereof.

network interface—any physical and/or logical device, system, and/or process capable of coupling an information device to a network. Exemplary network interfaces comprise a telephone, cellular phone, cellular modem, telephone data modem, fax modem, wireless transceiver, Ethernet card, cable modem, digital subscriber line interface, bridge, hub, router, or other similar device, software to manage such a device, and/or software to provide a function of such a device.

next—immediately following in an ordering.

norm—a vector function that assigns a positive size to all vectors of a vector space.

obtain—to receive, get, take possession of, procure, acquire, calculate, determine, and/or compute.

operate—to perform a function and/or to work.

optimal deformation—a most desirable as compared to other alternative movements for adjusting a position of a first image and/or structure comprised in first the image to align the first image with a second image.

optimizing—improving.

originate—to give rise to and/or initiate.

over—with reference to.

patient—a human or other type of animal under supervision for health care purposes.

physiological structure—an anatomical part of patient that comprises bone and soft tissue, such as a torso and/or leg; a hierarchy and/or placement of objects in a patient; and/or a manner in which body parts of a patient are organized and/or form a whole.

pixel—a smallest element of an image, and/or a two-dimensional representation thereof that can be individually processed in a video display system.

plurality—the state of being plural and/or more than one.

point—(n.) a defined physical and/or logical location in at least a two-dimensional system and/or an element in a geometrically described set and/or a measurement or representation of a measurement having a time coordinate and a non-time coordinate.

predetermined—determine, decide, or establish in advance.

prior—preceding in time.

probability—a quantitative representation of a likelihood of an occurrence.

processor—a hardware, firmware, and/or software machine and/or virtual machine comprising a set of machine-readable instructions adaptable to perform a specific task. A processor can utilize mechanical, pneumatic, hydraulic, electrical, magnetic, optical, informational, chemical, and/or biological principles, mechanisms, signals, and/or inputs to perform the task(s). In certain embodiments, a processor can act upon information by manipulating, analyzing, modifying, and/or converting it, transmitting the information for use by an executable procedure and/or an information device, and/ or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein. A processor can reside on and use the capabilities of a controller.

project—to calculate, estimate, or predict.

provide—to furnish, supply, give, convey, send, and/or make available.

reach—to arrive at.

receive—to gather, take, acquire, obtain, accept, get, and/or have bestowed upon.

recommend—to suggest, praise, commend, and/or endorse.

rectangular mesh—a predetermined grid dividing an image into a plurality of approximately boxlike neighborhoods containing a predetermined number of whole and/or fractional pixels.

reference—an indicator that provides a value and/or orientation relative to something else.

refine—to make more precise.

reflect—to indicate.

region-based, intensity invariant similarity measurement—a measurement indicative of how well two images match, the measurement associated with a predetermined portion of each of the two images, the measurement not directly affected by a brightness of the predetermined portion of each of the two images.

regularization parameter—a determined weighting value adapted to control strength of prior regularization terms.

related—connected to and/or associated with.

relative—considered with reference to and/or in comparison to something else.

render—to display, annunciate, speak, print and/or otherwise make perceptible to a human, for example as data, commands, text, graphics, audio, video, animation, and/or hyperlinks, etc., such as via any visual, audio, and/or haptic means, such as via a display, monitor, printer, electric paper, ocular implant, cochlear implant, speaker, etc.

repeat—to do and/or perform again.

repeatedly—again and again; repetitively.

request—(v.) to express a need and/or desire for; to inquire and/or ask for. (n.) that which communicates an expression of desire and/or that which is asked for.

resolution—a degree of sharpness of an image.

resolution layer—a layer of a plurality of layers comprised by a Gaussian Pyramid.

said—when used in a system or device claim, an article indicating a subsequent claim term that has been previously introduced.

search—to look thoroughly in order to find something.

second—following a first thing in an ordering.

select—to make and/or indicate a choice and/or selection from among alternatives.

set—a related plurality of predetermined elements; and/or one or more distinct items and/or entities having a specific common property or properties.

share—to use jointly.

sharpness—acuteness.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

similarity—resemblance.

size—dimensions, proportions, magnitude, amount, and/or extent.

smaller than—lower in magnitude as compared to something else.

soft tissue layer—a representation of soft tissue, the representation substantially devoid of a representation of bone.

source—original.

spectrum—a continuum of entities, as light waves or particles, ordered in accordance with the magnitudes of a common physical property.

statistical properties—characteristics of sets of measured values. Statistical properties can comprise, for example, mean, median, mode, variance, standard deviation, weighted average, running average, etc.

step—one of a series of actions, processes, or measures taken to achieve a goal.

store—to place, hold, retain, enter, and/or copy into and/or onto a machine-readable medium.

subpixel accuracy—resolution of an image to a degree of less than a pixel in size.

subpixel search—searching in the solution space with a search step size less than a pixel to attempt to find an optimal solution that minimizes an objective functional, substantially—to a considerable, large, and/or great, but not necessarily whole and/or entire, extent and/or degree.

system—a collection of mechanisms, devices, data, and/or instructions, the collection designed to perform one or more specific functions.

target—a destination.

term—a member comprised by a mathematical representation.

terminate—to end.

third—following a second thing in an ordering.

threshold—a point that when exceeded produces a given effect or result.

through—in one side and out the opposite or another side of, across, among, and/or between.

time interval—a quantity and/or finite amount of time between two specified instants, events, and/or states.

transformation—a change in form, appearance, nature, and/or character.

transmit—to provide, furnish, supply, send as a signal, and/or to convey (e.g., force, energy, and/or information) from one place and/or thing to another.

until—up to a time when.

update—to change.

user interface—a device and/or software program for rendering information to a user and/or requesting information from the user. A user interface can include at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

utilize—to use and/or put into service.

value—a measured, assigned, determined, and/or calculated quantity or quality for a variable and/or parameter.

vector—an expression characterized by a magnitude and a direction.

via—by way of and/or utilizing.

weight—a value indicative of importance.

weighting—a measure of importance.

where—in a situation or position.

wherein—in regard to which; and; and/or in addition to.

whether—a conjunction used to introduce the first of two or more alternatives.

within—inside.

x-ray—electromagnetic radiation of non-nuclear origin within the wavelength interval of approximately 0.1 to approximately 100 Angstroms.

Note

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, performed by multiple entities, and/or performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Accordingly, the descriptions and drawings are to be regarded as illustrative in nature, and not as restrictive.

What is claimed is:

1. A method comprising a plurality of activities comprising:

receiving a first image of a predetermined physiological structure of a patient, said first image originated from an X-ray device operated at a first energy spectrum, said first image originated during a first time interval;

receiving a second image of said predetermined physiological structure of said patient, said second image originated from said X-ray device operated at a second energy spectrum, said second image originated during a second time interval, said second time interval distinct from said first time interval;

automatically determining an initial estimate of a movement of said patient in said second time interval relative to said first time interval via a corner matching based registration, said corner matching based registration determined via:

defining a first Gaussian pyramid associated with said first image and a second Gaussian pyramid associated with said second image, said first Gaussian pyramid comprising a plurality of layers, said second Gaussian pyramid comprising a plurality of layers;

calculating a first corner strength map associated with said first image;

calculating a second corner strength map associated with said second image;

initializing a rectangular mesh associated with each layer of said first Gaussian pyramid;

for each control point in each rectangular mesh on a lowest resolution layer, determining a point with a largest corner strength in a defined neighborhood and define said point with said largest corner strength as said control point;

for each control point of each mesh on a lowest resolution layer in said first Gaussian pyramid, determining a corresponding control point in a corresponding layer in said second Gaussian pyramid; and generating a corresponding mesh on each layer of said second Gaussian pyramid to each mesh associated with each layer of said first Gaussian pyramid;

automatically determining an improved estimate of said movement of said patient in said second time interval relative to said first time interval based upon said initial estimate of said movement, said improved estimate obtained via an iterative hierarchical structured intensity comparison between said first Gaussian pyramid and said second Gaussian pyramid, said iterative hierarchical structured intensity comparison comprising, from a lowest resolution layer to a highest resolution layer of said first Gaussian pyramid and said second Gaussian pyramid:

defining a region-based, intensity invariant similarity measurement between said first image and said second image;

estimating an optimal deformation, associated with each control point, that attempts to maximize a similarity between said first image and said second image by searching within a neighborhood of each control point;

map an adjusted mesh of each layer to a next higher resolution layer to obtain an initial control point associated with said next higher resolution layer; and repeat said automatically determining said improved estimate activity for each resolution layer until said highest resolution layer is aligned;

achieving subpixel accuracy by searching within said neighborhood associated with each control point by utilizing a resolution level step size smaller than approximately one pixel on said highest resolution layer;

based on said estimated optimal deformation for each control point, automatically estimating a soft-tissue layer image and a bone layer image of said predetermined physiological structures of said patient; and automatically rendering said estimated soft-tissue layer image and said estimated bone layer image of said predetermined physiological structures of said patient.

2. A method comprising:

automatically determining a renderable image of a predetermined physiological structure of a patient, said renderable image determined based upon a first image of said predetermined physiological structure of said patient, said first image originated from an X-ray device operated at a first energy spectrum, said first image originated during a first time interval, said renderable image based upon a second image of said predetermined physiological structure of said patient, said second image originated from said X-ray device operated at a second energy spectrum, said second image originated during a second time interval, said second time interval distinct from said first time interval, said renderable image determined via an estimate of a movement of said patient in said second time interval relative to said first time interval, said movement estimated via a corner matching based registration, said corner matching based registration based upon a first Gaussian pyramid associated with said first image and a second Gaussian pyramid associated with said second image, said first Gaussian pyramid comprising a plurality of layers, said second Gaussian pyramid comprising a plurality of layers, said estimated movement refined via a mapped adjusted mesh of each layer of said plurality of layers, said plurality of layers iteratively mapped to obtain an initial control point associated with each next higher resolution level beginning at a lower layer and continuing through each of said plurality of layers of said first Gaussian pyramid and each of said plurality of layers of said second Gaussian pyramid until a highest resolution level of each of said first Gaussian pyramid and said second Gaussian pyramid is reached.

3. The method of claim 2, further comprising:

achieving a subpixel accuracy of said movement of said patient via a subpixel level search.

4. The method of claim 2, further comprising:

defining said first Gaussian pyramid associated with said first image and said second Gaussian pyramid associated with second image.

5. The method of claim 2, further comprising:

automatically calculating a corner strength map associated with said first image.

6. The method of claim 2, further comprising:

automatically calculating a corner strength map associated with said second image.

7. The method of claim 2, further comprising:

automatically initializing a rectangular mesh associated with each layer of said first Gaussian pyramid.

8. The method of claim 2, further comprising:

automatically initializing a rectangular mesh associated with each layer of said first Gaussian pyramid;

for each control point in each rectangular mesh on a lowest resolution layer of said first Gaussian pyramid, automatically determining a point with a largest corner strength in a defined neighborhood and define said point with said largest corner strength as said control point;

for each control point of each mesh in said lowest resolution layer in said first Gaussian pyramid, automatically determining a corresponding control point in a corresponding layer in said second Gaussian pyramid; and automatically generating a corresponding mesh on said lowest resolution layer of said second Gaussian pyramid to each mesh associated with each layer of said first Gaussian pyramid.

9. The method of claim 2, further comprising:
automatically estimating said movement of said patient in said second time interval relative to said first time interval via an iterative hierarchical structured intensity comparison between said first Gaussian pyramid and said second Gaussian pyramid.

10. The method of claim 2, further comprising:
defining a region-based, intensity-invariant similarity measurement between said first image and said second image.

11. The method of claim 2, further comprising:
automatically estimating an optimal deformation, associated with each control point, that attempts to maximize a similarity between said first image and said second image by searching within a neighborhood of each control point.

12. The method of claim 2, further comprising:
automatically mapping said adjusted mesh of each layer to a next higher resolution layer to obtain an initial control point associated with said next higher resolution layer.

13. The method of claim 2, further comprising:
automatically terminating an estimation of said movement of said patient in said second time interval relative to said first time interval if said next higher resolution level is a resolution level beyond a predetermined resolution level.

14. The method of claim 2, further comprising:
achieving subpixel accuracy by searching within a neighborhood associated with each control point by utilizing a resolution level step size smaller than approximately one pixel.

15. The method of claim 2, wherein a movement between a given layer in said first Gaussian pyramid and a corresponding layer in said second Gaussian pyramid is determined by attempting to minimize a functional:

$$\arg\min_{T^i}\left\{-CC(I_1^i, T^i(I_2^i)) + \lambda \sum_m \sum_n \left\|T^i(m, n) - \overline{T}_0^i(m, n)\right\|^2\right\}$$

where:
T is a transformation indicative of said movement of said patient in said second time interval relative to said first time interval;
CC is a correlation coefficient;
$I_1^i$ is an image associated with an $i^{th}$ layer of said first Gaussian pyramid based upon said first image;
$I_2^i$ is an image associated with an $i^{th}$ layer of said second Gaussian pyramid based upon said second image;
$T^i$ is a transformation indicative of a determined said movement of said patient in said second time interval relative to said first time interval associated with an ith layer of said first Gaussian pyramid and said second Gaussian pyramid;
$\lambda$ is a regularization parameter,
m and n are indices of pixels in an ith layer of said first Gaussian pyramid; and
$T_0$ is an initial estimate of said transformation indicative of said movement of said patient in said second time interval relative to said first time interval.

16. The method of claim 2, wherein said movement is estimated via evaluating a region-based, intensity-invariant similarity measurement based on an equation:

$$CC = \frac{\sum_m \sum_n (I_1(m, n) - \overline{I}_1) * (I_2(m, n) - \overline{I}_2)}{\sqrt{\sum_m \sum_n (I_1(m, n) - \overline{I}_1)^2 \sum_m \sum_n (I_2(m, n) - \overline{I}_2)^2}}$$

where:
CC is a correlation coefficient between predetermined neighborhoods of said first image and said second image;
$I_1$ is a target image;
$I_2$ is a source image;
$\overline{I}_1$ is an average intensity associated with said target image;
$\overline{I}_2$ is an average intensity associated with said source image; and
m and n are pixel indices.

17. The method of claim 2, wherein a determination of said adjusted mesh of a lowest resolution layer of said first Gaussian pyramid and said second Gaussian pyramid comprises calculating a corner strength map.

18. A non-transitory machine-readable medium comprising machine instructions for activities comprising:
automatically determining a renderable image of a predetermined physiological structure of a patient, said renderable image determined based upon a first image of said predetermined physiological structure of said patient, said first image originated from an X-ray device operated at a first energy spectrum, said first image originated during a first time interval, said renderable image based upon a second image of said predetermined physiological structure of said patient, said second image originated from said X-ray device operated at a second energy spectrum, said second image originated during a second time interval, said second time interval distinct from said first time interval, said renderable image determined via an estimate of a movement of said patient in said second time interval relative to said first time interval, said movement estimated via a corner matching based registration, said corner matching based registration based upon a first Gaussian pyramid associated with said first image and a second Gaussian pyramid associated with said second image, said first Gaussian pyramid comprising a plurality of layers, said second Gaussian pyramid comprising a plurality of layers, said estimated movement refined via a mapped adjusted mesh of each layer of said plurality of layers, said plurality of layers iteratively mapped to obtain an initial control point associated with each next higher resolution level beginning at a lower layer and continuing through each of said plurality of layers of said first Gaussian pyramid and each of said plurality of layers of said second Gaussian pyramid until a highest resolution level of each of said first Gaussian pyramid and said second Gaussian pyramid is reached.

19. A system comprising:
a processing means for automatically determining a renderable image of a predetermined physiological structure of a patient, said renderable image determined based upon a first image of said predetermined physiological structure of said patient, said first image originated from an X-ray device operated at a first energy spectrum, said first image originated during a first time interval, said renderable image based upon a second image of said predetermined physiological structure of said patient, said second image originated from said X-ray device operated at a second energy spectrum, said second image originated during a second time interval, said second time interval distinct from said first time interval, said renderable image determined via an estimate of a movement of said patient in said second time interval relative to said first time interval, said movement estimated via a corner matching based registration, said corner matching based registration based upon a first Gaussian pyramid associated with said first image and a second Gaussian pyramid associated with said second image, said first Gaussian pyramid comprising a plurality of layers, said second Gaussian pyramid comprising a plurality of layers, said estimated movement refined via a mapped adjusted mesh of each layer of said plurality of layers, said plurality of layers iteratively mapped to obtain an initial control point associated with each next higher resolution level beginning at a lower layer and continuing through each of said plurality of layers of said first Gaussian pyramid and each of said plurality of layers of said second Gaussian pyramid until a highest resolution level of each of said first Gaussian pyramid and said second Gaussian pyramid is reached; and a user interface adapted to render said renderable image.

* * * * *